United States Patent [19]

Hope

[11] Patent Number: Plant 5,668

[45] Date of Patent: Feb. 18, 1986

[54] KALANCHOE PLANT NAMED TIJUANA

[75] Inventor: Claude Hope, Cartago, Costa Rica

[73] Assignee: Pan American Plant Company, Parrish, Fla.

[21] Appl. No.: 594,488

[22] Filed: Mar. 27, 1984

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Schwartz, Jeffery, Schwaab, Mack, Blumenthal & Evans

[57] ABSTRACT

A new and distinct cultivar of Kalanchoe plant named Tijuana characterized by its bright rose red flower color and floriferous habit, compact and freely branching growth habit, and by its adaptability to production in 10–15 cm. pots.

1 Drawing Figure

The present invention relates to a new and distinctive cultivar of Kalanchoe plant, botanically known as Kalanchoe, named Tijuana.

The new cultivar was referred to during the selection process by the designation (Swiss Rose 2-1-3 × Tom Thumb Yellow -1-1)-1 × (Red Glow 2-1-3 × Vulcan 5-6-1-11-2)-4)-2-1, and is a product of a planned breeding program. Tijuana was later recoded KLV80-57R when received by Pan American Plant Co., West Chicago, Ill. in 1980. The basic objective of the breeding program was to create a new Kalanchoe cultivar having brilliant red flower color, compact habit, and the ability to produce commercially acceptable quality in a year round Kalanchoe program.

The new cultivar was originated from a self-pollination of (Swiss Rose 2-1-2 × Tom Thumb Yellow -1-1)-1 × (Red Glow 2-1-3 × Vulcan 5-6-1-11-2)-4)-2, made in a controlled breeding program at Linda Vista S.A., Cartago, Costa Rica.

Tijuana was discovered and selected by me or a technician working under my direction, as a flowering plant within the progeny of the stated self in the field of seedlings in Cartago, Costa Rica. Asexual reproduction of the new cultivar by stem cuttings, as performed by me at Pan American Plant Co., West Chicago, Ill. and Parrish, Fla., has demonstrated that the combination of characteristics as herein disclosed for the new cultivar are firmly fixed and are retained through successive generations of asexual reproduction.

Tijuana has not been observed under all possible environmental conditions. The phenotype may vary significantly with variations in environment such as temperature, light intensity and day length. The following observations, measurements and values describe the new cultivar as grown in Parrish, Fla., under greenhouse conditions which closely approximate those generally used in commercial practice.

The following traits have been repeatedly observed and are determined to be basic characteristics of Tijuana, which in combination distinguish this Kalanchoe as a new and distinct cultivar:

(1) Outstanding bright rose red flower color.

(2) Very compact habit, and average growth rate as compared to other cultivars.

(3) Freely branching, with shoots formed at every node.

(4) Suitable for production in 10–15 cm. pots, and flowering from 12 weeks under favorable conditions to 14 weeks under less favorable conditions.

(5) Highly floriferous, with numerous flowers formed at every shoot.

(6) To reduce peduncle elongation after flower initiation, plants can be treated with B-9.

(7) Very thin band of red on leaf margins when grown under high light and temperature conditions.

The new cultivar is most similar to Acapulco, disclosed in my application Ser. No. 496,283, filed May 19, 1983. Tijuana is principally distinguished from Acapulco by its rose red flower color and less apparent red leaf margin under high light temperatures. The flower color of Acapulco is in the red-purple range.

The accompanying photographic drawing shows a typical specimen plant of the new cultivar. The colors appearing in the photograph are as true as possible with color illustrations of this type.

In the following description, color references are made to The Royal Horticultural Society Colour Chart (R.H.S.), except where general colors of ordinary significance are referred to. Color values are taken under 7000 ft. candles of natural light at approximately 10:30 A.M. in Parrish, Fla.

Botanical classification: Kalanchoe, cv. Tijuana.

Parentage: Self-pollination of the cultivar (Swiss Rose 2-1-3 × Tom Thumb Yellow -1-1)-1 × (Red Glow 2-1-3 × Vulcan 5-6-1-11-2)-4)-2.

Propagation: The new cultivar holds its distinguishing characteristics through successive propagations by leaf cuttings and by division of shoots.

A. *Type cutting.*—Tip cuttings with stems up to 2 cm. long.

B. *Time to root.*—10 days at 21° C., summer to 14 days 21° C. winter.

C. *Rooting habit.*—Fibrous, many very fine roots.

Plant description:

A. *Form.*—Upright, short, compact growth; scheduling practices can produce small plants in 10 cm. pots or large plants in 15 cm. pots.

B. *Habit of growth.*—Average growth rate for this type of plant. Shoots are formed at every node.

C. *Foliage description.*—Leaves simple, opposite and generally symmetrical; edged with red on margin when grown in high light and temperatures. (1) Size: Average full grown leaf of a flowering plant in a 10 cm. pot is 65–80 mm. long and 50–75 mm. wide. Plants in larger pots have larger full grown leaves. (2) Shape: Ovate. Apex obtuse to acute base truncate. (3) Texture: Glabrous, coriaceous, succulent. (4) Margin: Crenate, irregular. (5) Color: Young foliage top side, 137C, under side, 137D. Mature foliage top side 137B, under side 137C.

Flowering description:

A. *Flowering habit.*—Inflorescence of each shoot is formed by dichotomous branching, starting with opening of terminal flower of main axis followed by terminal flowers of the side branches of the inflorescence. Opening of new buds will continue for 2 months or more. Individual flowers last two weeks or more after opening.

B. *Natural flowering season.*—January. Flowering time under controlled daylength at 32° C. in summer is 14 weeks; in winter at 21° C., 12 weeks. Flowering time depends on temperature, light intensity and other growing conditions.

C. *Flower buds.*—Oblong, developing to tubular as petals mature. Sheathed with 4 green sepals. Corolla at maturity about 15 mm. long. (1) Size: Up to 15 mm. long. (2) Shape: Oblong. (3) Rate of opening: Normal.

D. *Flower borne.*—Compound dichasial cyme on strong peduncles. Peduncle length depends on growing conditions and B-9 applications. Pedicels up to 5 mm. long.

E. *Quantity of flowers.*—Very floriferous with new buds continuing to develop.

F. *Petals.*—(1) Shape: Obovate, apex cuspidate. (2) Color: Top side when opening, 53C, fading to 53D; under side 55C. (3) Number and size of petals: 4; united in corolla; petals 5 mm. in diameter, total flower diameter 15 mm.

G. *Reproductive organs.*—(1) Stamens: 8 in number. (a) Anther shape: Flat, elliptical. (b) Filament color: Yellow. (c) Pollen color: Yellow. (2) Pistils: (a) Stigma shape: Flat crystalline. (b) Style color: Greenish-white. (c) Ovaries: 4 celled, 7 mm. long, green.

Disease resistance: No known Kalanchoe diseases observed to date.

General observations: Tijuana is characterized by its bright rose red flower color, compact and freely branching habit, and medium green foliage that is edged in red when growth under high light conditions. Tijuana has an average 12 week flowering response, and is adaptable to production in 10–15 cm. pots.

I claim:

1. A new and distinct cultivar of Kalanchoe plant named Tijuana, as described and illustrated, and particularly characterized by its bright rose red flower color and floriferous habit, compact and freely branching growth habit, and by its adaptability to production in 10–15 cm. pots.

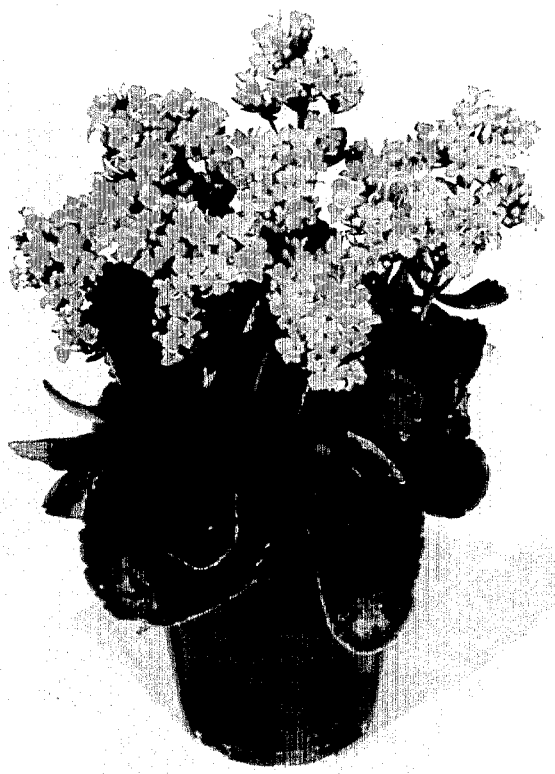

* * * * *